United States Patent [19]

Kaplan

[11] Patent Number: 5,614,222
[45] Date of Patent: Mar. 25, 1997

[54] STABLE AQUEOUS DRUG SUSPENSIONS AND METHODS FOR PREPARATION THEREOF

[76] Inventor: Milton R. Kaplan, 1523 Hawks Meadow, San Antonio, Tex. 78248

[21] Appl. No.: 329,153

[22] Filed: Oct. 25, 1994

[51] Int. Cl.⁶ ........................................... A61K 9/14
[52] U.S. Cl. .................... 424/489; 424/491; 424/494
[58] Field of Search .......................... 424/489, 491, 424/494

[56] References Cited

U.S. PATENT DOCUMENTS 4,166,800 9/1979 Fong ........................................ 424/494
4,818,542 4/1989 DeLuca et al. ......................... 424/491
5,288,502 2/1994 McGinity et al. ...................... 424/491

*Primary Examiner*—Paul R. Michl
*Assistant Examiner*—William E. Benston, Jr.

[57] ABSTRACT

Finely divided drug particles are coated with a lipid or bioadhesive polymer to form microspheres having a particle size of about 550 micrometers or less, and coated with two or more enteric coatings, at least one of which is water insoluble, to form microcapsules. The resultant microcapsules can be suspended in an aqueous solution to form stable oral doses of the drug.

9 Claims, 3 Drawing Sheets

STABLE AQUEOUS DRUG SUSPENSIONS AND METHODS FOR PREPARATION THEREOF

FIELD OF THE INVENTION

This invention relates to aqueous suspensions of encapsulated drugs having improved stability during storage, but which are designed for systemic environmentally-activated release at desired post-administration times and places, and processes for making such suspensions.

BACKGROUND OF THE INVENTION

Drugs such as amoxicillin, ampicillin, penicillin V and erythromycin are antibacterial drugs which are available for oral dispensation in a gelatin capsule containing a specified dosage amount of the drug. For patients who have difficulty swallowing capsules, e.g., the very young and the very old, the drugs can be suspended in an aqueous solution, such as a sugar type syrup. However, the aforementioned drugs are quite unstable in water, even when stored at temperatures of about 4° C., and very unstable at room temperature. Thus the drug solutions or suspensions have a very short shelf life, even at low temperatures. Further, they have an unpleasant taste which makes them unpalatable.

Beta-lactam antibiotics are orally inactive, and must be combined with an enhancer to promote their absorption into the body of the patient. Such enhancers are known, for example see U.S. Pat. No. 4,525,339, and include aliphatic fatty acids or acid glycerides. The fatty acids are generally $C_2$ to $C_{18}$ fatty acids, which can be straight or branched chain, saturated or unsaturated, their mono-, di- or triglycerides or mixtures thereof, and can also be partial or total esters of propylene glycol, polyethylene glycol and carbohydrates of $C_2$ to $C_{12}$ fatty acids and pharmaceutically acceptable esters and ethers of said glyceride. Encapsulating the drug in the enhancer is known also.

It would be quite advantageous to be able to formulate the above-described drugs, in a liquid-deliverable form, which would, nevertheless, be stable over the course of long term storage, i.e., for up to about 18 months, even at room temperature. To achieve this elusive objective without compromising the efficacy of the drugs, the drugs would have somehow to be isolated from the water in the storage/delivery medium, yet be released at the appropriate time and in the desired systemic environment of a recipient's body. In satisfying these objectives, drugs could be coated uniformly and completely with a water-impervious coating. In order for the encapsulated drug particles to stay suspended in an aqueous solution or emulsion for administration in liquid form, the individual particle size of the encapsulated drug particles would have to be very small, on the order of 1500 micrometers or less; otherwise the drug particles would settle out of the solution or suspension, and the dosage would be inaccurate.

Therefore, a suitable coating or encapsulant material must be impervious to water (to withstand long-term storage), but for efficacious patient treatment must dissolve in the stomach or other appropriate portion of the digestive tract, depending on the drug to be administered and the dosage required. Coatings having particular solubility characteristics can be used to provide controlled or delayed release of the drug in the patient.

Unfortunately, no one encapsulant coating is known to date that is effective to carry out all of the above-described objectives. Thus there is a need to be able to apply more than one encapsulant material, successively and uniformly, over very small particle size granules of the drug to be administered. Thus, it would be highly desirable to provide a practicable method for preparing small microspheres, on the order of about 500 micrometers, at the center of each of which lie individual drug particles. Each drug particle is encapsulated by successive encapsulants, each of a material which dissolves in a particular systemic environment in order to expose the next, more interior encapsulant layer for subsequent reaction at a distinctly new systemic environment, and ultimately for exposing the drug particle at the appropriate time and systemic loci.

SUMMARY OF THE INVENTION

Applicant has discovered that it is possible and practical to manufacture microspheres (or "microcapsules") at the center of which lie drug particles of up to about 550 microns in size, each drug particle being encapsulated by a succession of uniform and completely encapsulating coatings of matrix material of a lipid or a bioadhesive polymer. At least one of the multiple coatings is impervious to moisture, to produce microcapsules which are insoluble in water at about neutral pH, but which are soluble at acid pH. The microcapsules have a maximum particle size of about 1500 micrometers so they will stay suspended in an aqueous solution. The microcapsules can be tailored to have other features, such as successive layers cf encapsulants having differing solubility characteristics.

The microspheres are made using high speed rotation, e.g., a rotating disc method, that forms uniform, spherical particles of the required size. The microspheres are encapsulated with two or more coatings having differing solubility characteristics. The resulting water impervious microcapsules can be admixed with aqueous solutions to form stable suspensions or mixtures that have a long shelf life in a concentration to provide dosage amounts of the drug that can be taken orally.

DETAILED DESCRIPTION OF THE INVENTION

The microspheres and microcapsules described in this invention can be prepared using a variety of methods, including but not limited to, a rotating disc system, spray drying, a centrifugal extrusion nozzle device, an air suspension cooler, phase separation and solvent evaporation. In the following paragraphs some of the procedures that can be used to prepare the microcapsules described hereinafter are set forth in detail. Variations will be known to those skilled in the art.

Figure 1:
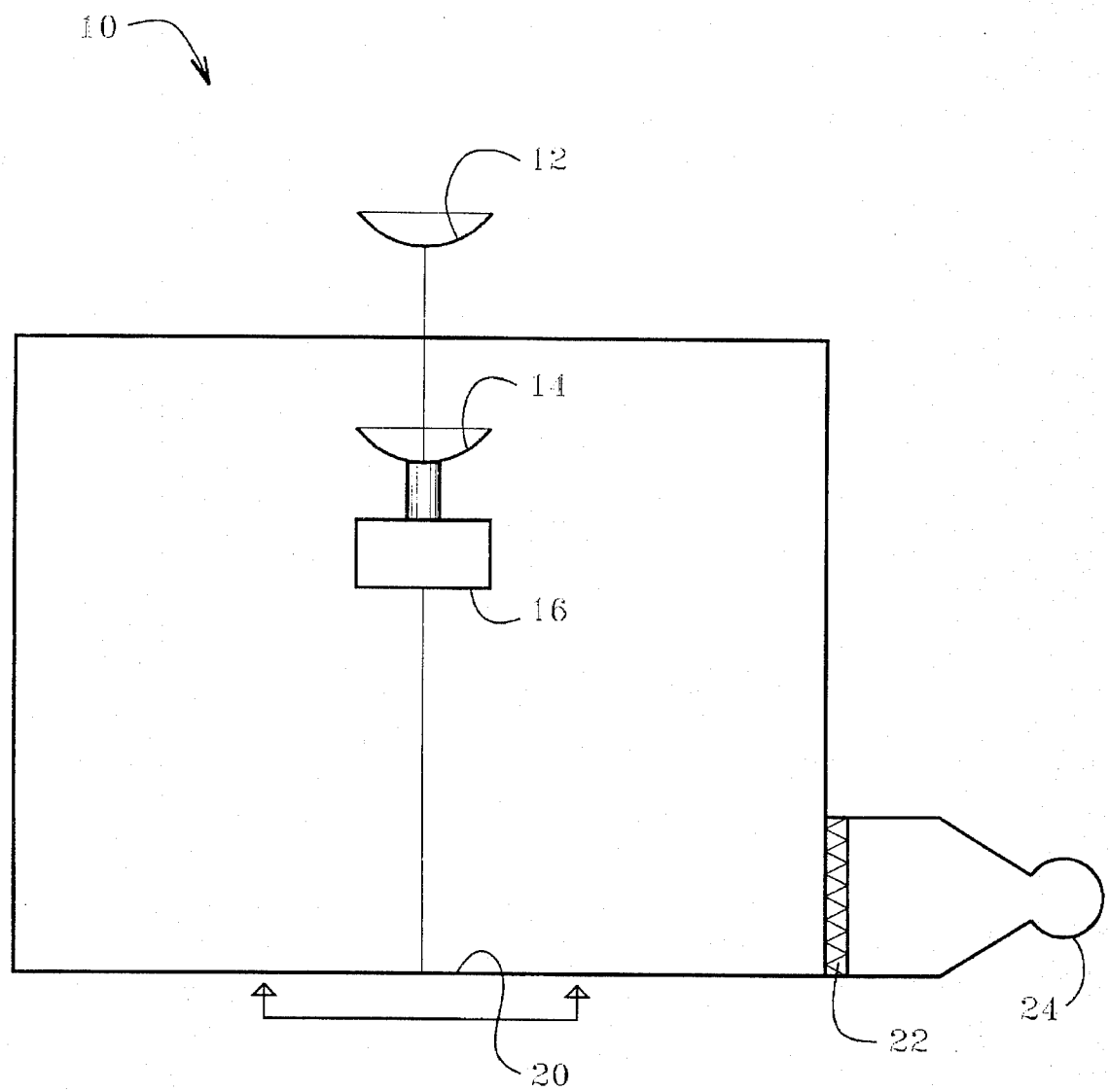
FIG. 1 is a cross sectional view of a high speed rotating disc system for preparing the microspheres of the invention.

Microspheres of the desired particle size, i.e., less than 550 micrometers, and preferably between about 250 to 500 micrometers, can be made using a high speed rotating disc system as shown in FIG. 1.

Referring to FIG. 1, the high speed rotating disc system 10 comprises an emulsion feed tube 12 which is situated over and feeds onto a rotating disc 14. The disc 14 is rotated by means of a motor 16. The disc 14 and the motor 16 are enclosed in a chamber 18. The chamber 18 serves to dry or cool and solidify the microspheres and to collect them in a collection area 20. The chamber 18 is also fitted with a filter 22 and an exhaust system 24. The disc 14 is situated some distance above the collection area 20 to allow time for solidification of the microspheres.

In operation, a slurry of the solid drug particles, which are finely divided below about 100 micrometers, and a suitable matrix, e.g., a lipid or bioadhesive composition, is fed to the feed tube 12 and dropped onto the rotating disc 14. Droplets or microspheres are thrown out from the periphery of the disc 14 due to the centrifugal forces developed by the high speed rotation of the disc 14, and fall by gravity to the collection area 20 of the chamber 18. The small spherical liquid droplets or microspheres are dried/cooled and solidified during this free fall, and are then collected. If desired, the microspheres can be sieved to collect a desired particle size distribution. For a disc about 4 inches in diameter rotating at about 2000 rpm, and a drug particle size of about 50 micrometers, the majority of the resultant microspheres have a particle size of about 105 to 500 micrometers. Control of the rotational speed of the disc 14 provides control over the size and size distribution of the microspheres.

Alternatively, and particularly suitable for hot melt matrix materials, microspheres can be formed in a centrifugal extrusion apparatus 110 as shown in FIG. 2. Referring to FIG. 2, the feed mixture or slurry of drug particles in the heated matrix material is fed through the center tube of a concentric feed tube 112 by means of a seal (not shown) to a rotating head 114 fitted with one or more nozzles 116. A rotating shaft 118 rotates the head 114 at high speed by means of a motor 119. A mechanical stirrer (not shown) can be used in the feed tank (not shown) prior to pumping through the feed tube 112 to provide continuous stirring of the drug particles in the hot melt matrix. As the head 114 rotates, the slurry of the drug in the matrix material flows through the inner orifice of the nozzle, creating a stream of the drug particles uniformly dispersed in the molten matrix material. This extruded rod breaks into individual particles due to the high speed rotation of the head 114. The coated drug particles are cooled and solidify to form the desired microspheres as they free fall into the collection area 120. The size of the resultant microspheres can be controlled and is dependent upon the feed rate, the speed of rotation of the head 114 and the size of the nozzle openings. Microsphere particle sizes of from about 250 to 500 micrometers can be made readily.

In order to form the microcapsules of the invention, the microspheres as prepared above are encapsulated in one or more coatings, at least one of which is water-impervious.

The microcapsules can be prepared using the apparatus as shown in FIG. 2, except using an additional feed line into the head 114. The slurry of the drug particles in the heated matrix material is fed through the center tube of the concentric teed tube 112. The desired encapsulant material and any additives are fed through a separate feed line to the outer tube 113 of the feed tube 112 to the head 114. The additional feed line is provided to supply the encapsulant material, e.g., a water impervious polymer dissolved in a solvent, as well as any optional materials desired such as colorants, flavorings, surfactants and other additives as desired. The slurry of the drug particles in the matrix material is fed along with the encapsulant material, to the head 114. The rotation of the head 114 causes the encapsulant or encapsulant mixture to flow through the outer orifice of the nozzle and the drug slurry to flow through the inner orifice of the nozzle, creating a rod of the drug slurry encased in a sheath of the encapsulant materials. If an organic solvent is used in the encapsulant, it is vaporized and can be collected through the exhaust (not shown) for disposal or, recycled as desired.

The microcapsules of the invention can also be made in a modified air suspension coater apparatus as shown in FIG. 3. The air suspension coater 210 comprises a chamber 212 fitted with an air distribution plate 216 through which an air stream passes. A feed line 220 for supplying the encapsulant material is connected to a hydraulic or pneumatic nozzle 224 which atomizes the encapsulant material into small droplets which coat the microspheres.

In operation, the microspheres 226 to be coated are fed through an entry port 228 in the chamber 212. An air stream supplied by means of a blower is fed into the chamber 212 and passes through the air distribution plate 216 to carry the microspheres smoothly past the head 224 for coating with encapsulant, and then up and over a coating partition 230 where the coated microspheres are dried and cooled during free fall back outside the coating partition 230 to begin another cycle past the nozzle 224. The nozzle 224 is designed to atomize the coating material to allow a uniform, thin coating to be applied. In the course of multiple passes of the microspheres past the nozzle 224, the encapsulant material uniformly coats the microspheres to the desired thickness. By changing the encapsulant materials which are fed to the nozzle 224, successive layers of desired encapsulant compositions are applied. Control of the air volume end temperature, atomizing conditions and rate of application ensures a high degree of uniformity of the coatings from batch to batch. Further, the closed system of the apparatus 210 provides excellent control of the conditions within the coater.

Virtually any non-liquid medicinal agent can be processed using Applicant's invention. However, the greatest benefit arises from processing drugs which are highly unstable in water and which would be more efficaciously or easily administered in an aqueous medium. This may be because of a patient's difficulty in taking tablets, or because of some other, more aesthetic characteristic of the drugs (chalkiness, bad taste). For these and other reasons as well, Applicant's invention particularly benefits those who administer and receive antibacterial drugs including erythromycin or erythromycin ethyl succinate, and the penicillins, their salts, esters and hydrates, such as amoxicillin trihydrate, ampicillin trihydrate, penicillin V potassium and the like. These drugs are unstable in water, are presently administered in tablet form, and are unpalatable to most patients if simply admixed into a syrup medium.

These drugs are supplied in solid form. If a drug is supplied in a larger particle sizes than are desired for processing according to Applicant's invention, milling can effectuate the desired particle sizes prior to coating with a lipid coating.

As used herein, the term lipid includes fatty acids, whether saturated or unsaturated, such as monobasic aliphatic carboxylic acids which form esters with glycerol or other alcohols to make fats, oils, waxes and other lipids. Also included are the esters and ethers of glycerides, the esters formed by reaction of the fatty acids with glycerol, such esters formed from pharmaceutically acceptable weak acids such as tartaric acid and its diacetyl derivative, acetic acid, ascorbic acid and citric acid, or one having a monophosphate group to yield the mono-phosphate ester. Suitable ethers are formed by reaction of the mono- or diglyceride with a functionally reactive lower alkyl, alkenyl, alkynyl, aryl or substituted aryl group to produce the corresponding pharmaceutically acceptable ether, as is known in the art. Polyhydric alcohols such as octanol or a carbohydrate polyol, e.g., sucrose, are also useful in the present invention.

The matrix material can also be a bioadhesive polymer that will provide a delayed release of the drug. The bioadhesive polymer attaches to the stomach lining or mucin coating of the stomach, where it hydrates and is absorbed, thereby releasing the drug particles.

Suitable bioadhesive polymers include adhesive materials such as gelatin, polycarbophil polymers, and Chitosan, commercially available from Protan of Norway. These matrix materials provide a delivery system which may provide a long acting dosage form by providing a reduced rate of emptying of the drug in the stomach, improve bioavailability of the drug, improved therapy, and increase the contact time of the drug in the desired absorption area.

The microspheres are made into microcapsules by means of one or more enteric coatings. The enteric coatings can be tailored to have the drug absorbed in the body as desired, but at least one layer of enteric coating must be water insoluble at normal pH. Most antibiotics are meant to be absorbed in the intestinal tract, and thus must be protected from the high acid content gastric fluid of the stomach. Thus successive coatings may be insoluble in highly acid environments, i.e., pH below about 5, but soluble in less acid environments, i.e. pH about 5.5 to 7.5 or higher.

Examples of known enteric coating materials useful herein include cellulose acetate phthalate, cellulose acetate trimellitate, hydroxypropyl methylcellulose phthalate, polyvinyl acetate phthalate, shellac, methacrylic acid and methacrylic acid esters and zein. Partially hydrogenated vegetable oils, stearic acid, hydrogenated tallow triglycerides, food grade metal stearates, tallow and mixtures thereof and the like are used as lipids, carriers and modifiers for the microspheres. Suitable partially hydrogenated vegetable oil material is commercially available as Durkee 17 and Durkee KLX from Van den Burgh. Emersol 6349 stearic acid is commercially available from Emory Industries. Hydrogenated tallow triglycerides are commercially available as Grocol 600-E from A. Gross and Co. Suitable tallow flakes are commercially available from Anderson Clayton/Hank Products, Inc. A series of methacrylic acid or methacrylic acid esters commercially available as EUDRAGIT coatings, trademarks of Rotim Pharma GmbH of Westerstadt, West Germany, have varying degrees of esterification, and are soluble at varying pH. Thus drugs which are meant to be absorbed in the small intestine will be encapsulated in a first enteric coating that is insoluble in water but soluble in acidic environment, e.g., the stomach, and a second enteric coating which is insoluble in the low pH gastric fluid of the stomach, but soluble in the less acid environment of the small intestine. For example, EUDRAGIT L-100 is insoluble at neutral pH but soluble at a pH less than 5.5; EUDRAGIT L-100-55 and L-30D are soluble at pH greater than. 5.5. Metal stearates incorporated into these shell materials can increase water repellency. Other enteric coatings are known which are less soluble and can provide release of the drug over time, as will be known to those skilled in the art.

To provide both water impermeability, protection of the drug in the stomach and release in the intestine, and delayed release in the intestine, a series of enteric coatings will be applied to the microspheres. The outer layer will be water insoluble at normal pH, but will dissolve in the stomach (pH less than. 5.5). The next layer will be insoluble at low pH in the stomach, but will dissolve and release the drug in the intestine (pH greater than 5.5). A third layer can provide delayed release until the drug enters the upper gastrointestinal tract, where the pH is higher again.

The enteric coatings are dissolved in an organic solvent, suitably one approved for medicinal use, such as acetone, methylene chloride, or the lower alcohols such a ethanol, or mixtures of such solvents, and applied to the microspheres as above. The organic solvents are removed by evaporation during the processing of the microcapsules.

The amount of coating applied to the microspheres is not critical, and can vary from 5 to 30% by weight of the microcapsule. It is important that the enteric coating be applied uniformly over the microsphere to ensure that the microspheres are protected from moisture, and that a given dosage of the drug will be released by the coatings at the appropriate portion and time in the digestive tract. Too thick a coating will delay dissolution of the coating and release of the drug.

The enteric coatings can also contain conventional additives such as suspending agents, emulsifying agents, essential oils, preservatives, flavoring or coloring agents and the like, as is known to one skilled in the art. Such additives can retain a desired texture, retard hydration or dehydration of the microsphere ingredients, and provide a uniform color and appearance.

The invention will be further described in the following examples, but the invention is not meant to be limited to the details thereof. In the examples, percent is by weight.

The actual erythromycin and erythromycin ethyl succinate content of the microspheres was determined by high pressure liquid chromatography (HPLC).

Actual amoxicillin trihydrate content in the microspheres was determined using an iodimetric titration method, see Code of Federal Regulations: Food and Drugs, Vol 21, Chap 1 Part 436.204 (1988), 291.

EXAMPLE 1

Using the rotating disc apparatus of FIG. 1, a slurry containing 30.0% of Erythromycin USP, 44.1% of Emersol 6349, 18.9% of Durkee 17 and 7.0% of aluminum stearate EA was heated to 180° F. and fed to the disc maintained at a temperature of 160° F.

The resultant microspheres had a particle size distribution of 4.3% particles of less than 105 microns; 84.9% particles of 105–250 microns; and 10.8% particles of 250–355 micrometers.

An assay of the microspheres having a particle size of 250–355 micrometers determined the actual Erythromycin content to be 20.9%.

EXAMPLES 2–13

The procedure of Example 1 was followed except varying the matrix composition and temperature. In these Examples, 30.0% of Erythromycin was employed. The data summarizing the matrix composition, the matrix temperature, particle size and weight % distribution obtained and the actual Erythromycin content in the microspheres are summarized below in Table I. In the Table, D17 represents Durkee 17; E6349 represents Emersol 6349; G 600-E represents Grocol 600-E; Zn St represents food grade zinc stearate; Mg St represents food grade magnesium stearate; Al St represents food grade aluminum stearate; and A 84K represents Atmul 84K.

TABLE I

| Example | Matrix Composition | Temp. °F. | Particle Size Micrometers | Weight % | Actual % Erythromycin |
|---|---|---|---|---|---|
| 2 | 70.0% D17 | 155 | 250–355 | 100 | 25.3 |
| 3 | 56.0% E6349 | 155 | 105–250 | 18.4 | 25.7 |
|   | 14.0% G600-E |   | 250–355 | 68.4 |   |
|   |   |   | 355–500 | 13.2 |   |
| 4 | 52.5% E6349 | 155 | 105–250 | 35.8 | 24.5 |
|   | 17.5% D17 |   | 250–355 | 64.2 |   |
| 5 | 50.4% E6349 | 180 | 105–250 | 35.7 | 24.5 |
|   | 12.6% G600-E |   | 250–355 | 64.3 |   |
|   | 7.0% Zn St |   |   |   |   |
| 6 | 44.1% E6349 | 180 | 105–250 | 61.6 | 21.3 |
|   | 18.9% D17 |   | 250–335 | 38.4 |   |
|   | 7.0% Zn St |   |   |   |   |
| 7 | 63.0% D17 | 190 | 105–250 | 38.1 | 20.9 |
|   | 7.0% Zn St |   | 250–355 | 61.9 |   |
| 8 | 50.4% E6349 | 190 | 105–250 | 71.4 | 26.5 |
|   | 12.6% G600-E |   | 250–355 | 28.6 |   |
|   | 7.0% Mg St |   |   |   |   |
| 9 | 44.1% E6349 | 190 | 105–250 | 52.9 | 27.3 |
|   | 18.9% D17 |   | 250–355 | 47.1 |   |
|   | 7.0% Mg St |   |   |   |   |
| 10 | 63.0% D17 | 190–200 | 105–250 | 23.4 | 27.3 |
|   | 7.0% Mg St |   | 250–355 | 55.8 |   |
|   |   |   | 355–500 | 20.8 |   |
| 11 | 50.4% E6349 | 180 | 105–250 | 83.0 | 21.3 |
|   | 12.6% G600-E |   | 250–355 | 17.0 |   |
|   | 7.0% Al St |   |   |   |   |
| 12 | 63.0% D17 | 190–200 | 105–250 | 57.1 | 26.5 |
|   | 7.0% Al St |   | 250–355 | 23.1 |   |
|   |   |   | 355–500 | 19.8 |   |
| 13 | 63.0% D17 | 190 | 105–250 | 25.8 | 27.3 |
|   | 7.0% A84K |   | 250–355 | 74.2 |   |
| Control | 100% D17 | 155 | <105 | 15.2 | — |
|   |   |   | 105–250 | 58.7 |   |
|   |   |   | 250–355 | 26.1 |   |

All of the microspheres were satisfactory.

EXAMPLE 14–22

The procedure for Examples 2–13 was followed except using 23% of Erythromycin. The data are summarized in Table II below, where the symbols are the same as for Table I.

TABLE II

| Example | Matrix Composition | Temp. °F. | Particle Size Micrometers | Weight % |
|---|---|---|---|---|
| 14 | 56.0% E6349 | 190 | 105–250 | 15.9 |
|   | 14.0% G600-E |   | 250–355 | 63.5 |
|   | 7.0% Zn St |   | 355–500 | 20.6 |
| 15 | 52.5% E6349 | 190 | 105–250 | 39.9 |
|   | 17.5% D17 |   | 250–355 | 60.1 |
|   | 7.0% Zn St |   |   |   |
| 16 | 70.0% D17 | 190 | 105–250 | 23.9 |
|   | 7.0% Zn St |   | 250–355 | 76.1 |
| 17 | 56.0% E6349 | 190 | 105–250 | 30.4 |
|   | 14.0% G600-E |   | 250–355 | 59.8 |
|   | 7.0% Al St |   | 355–500 | 9.8 |
| 18 | 52.5% E6349 | 190 | 105–250 | 67.5 |
|   | 17.5% D17 |   | 250–355 | 32.5 |
|   | 7.0% Al St |   |   |   |
| 19 | 70.0% D17 | 190–200 | <105 | 8.2 |
|   | 7.0% Al St |   | 105–250 | 46.9 |
|   |   |   | 250–355 | 44.9 |
| 20 | 56.0% E6349 | 190 | 105–250 | 67.0 |
|   | 14.0% G600-E |   | 250–355 | 33.0 |
|   | 7.0% Mg St |   |   |   |
| 21 | 52.5% E6349 | 190 | 105–250 | 58.9 |
|   | 17.5% D17 |   | 250–355 | 41.1 |
|   | 7.0% Mg St |   |   |   |
| 22 | 70.0% D17 | 190 | 105–250 | 10.4 |
|   | 7.0% Mg St |   | 250–355 | 71.4 |
|   |   |   | 355–500 | 18.2 |

All of the microspheres were satisfactory.

EXAMPLES 23–34

Figure 2:
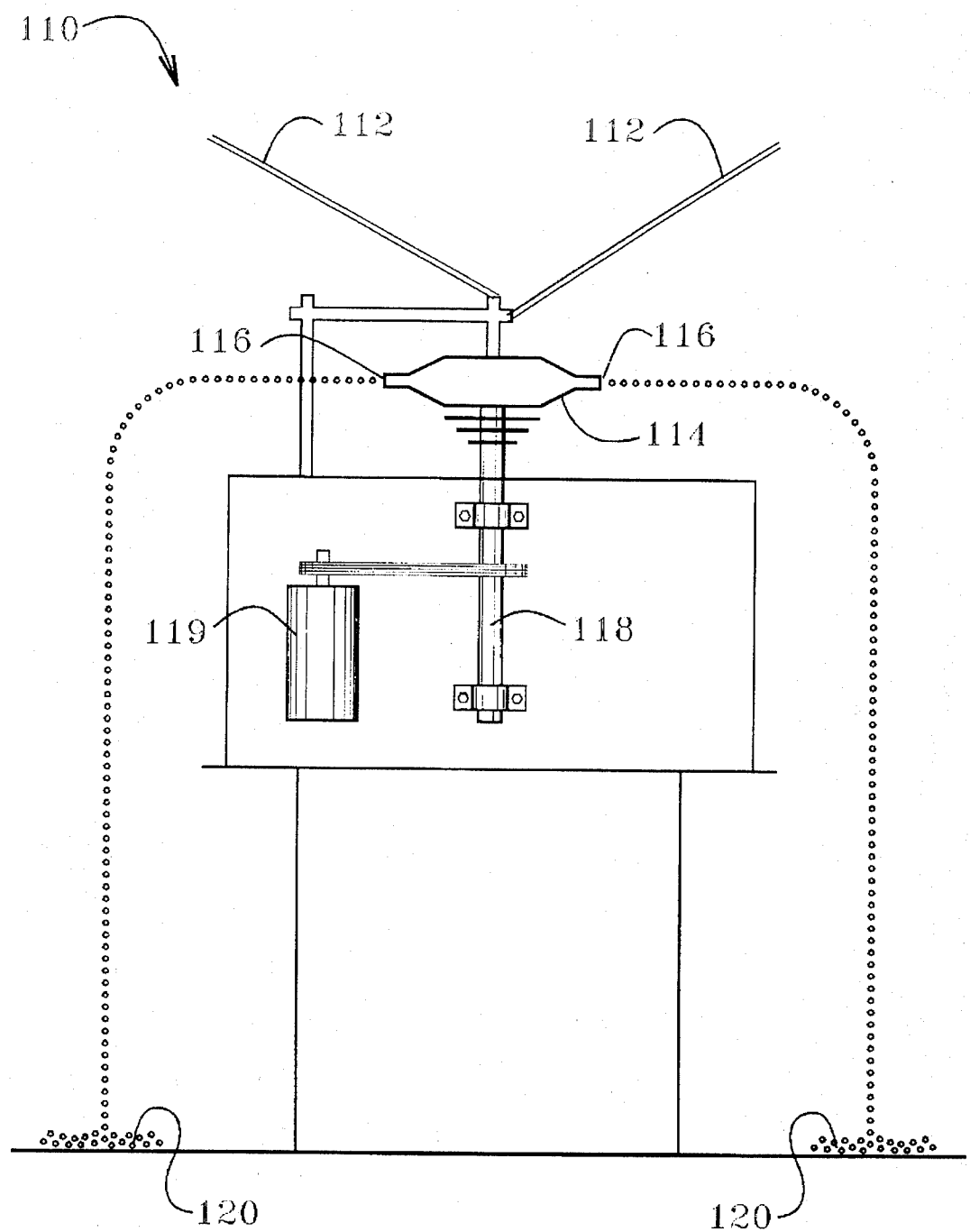
FIG. 2 is a cross sectional view of a centrifugal extrusion apparatus also used for preparing the microspheres and microcapsules of the invention.

Using the apparatus of FIG. 2 at a head speed of 2000 rpm, a head temperature of 190° F. and a shell composition temperature of 180° F., a slurry of the drug in a matrix material was encapsulated with a single layer of various encapsulant compositions to produce microcapsules. Equal amounts by weight of the drug slurry and encapsulant were employed; thus the theoretical amount of Erythromycin was 15% in the microcapsules, which were sieved to collect a particle size of 250–500 micrometers for analysis. The data are summarized in Table III below where the symbols are the same as for Table I and N 060 represents Neutrene 060 triglycerides.

TABLE III

| Example | Encapsulant Composition | Slurry Composition | Actual Erythromycin |
|---|---|---|---|
| 23 | 90% D17<br>10% Zn St | Ex3 | 8.7 |
| 24 | 80% E6349<br>20% G600-E | Ex3 | 9.5 |
| 25 | 80% E6349<br>20% G600-E | Ex2 | 5.4 |
| 26 | 100% D17 | Ex2 | 6.1 |
| 27 | 90% D17<br>10% Zn St | Ex2 | 5.6 |
| 28 | 90% D17 | Ex2 | 6.1 |

TABLE III-continued

| Example | Encapsulant Composition | Slurry Composition | Actual Erythromycin |
|---|---|---|---|
| | 10% Mg St | | |
| 29 | 100% D17 | Ex3 | — |
| 30 | 90% D17<br>10% Mg St | Ex3 | — |
| 31 | 80% E6349<br>20% N060 | 56.0% E6349<br>14.0% N060<br>30% Erythromycin | 6.7 |
| 32 | 100% D17 | 56.0% E6349<br>14.0% N060<br>30% Erythromycin | — |
| 33 | 90% D17<br>10% Zn St | 56.0% E6349<br>14.0% N060<br>30% Erythromycin | — |
| 34 | 90% D17<br>10% Mg St | 56.0% E6349<br>14.0% N060<br>30% Erythromycin | — |

EXAMPLES 35–47

Figure 3:
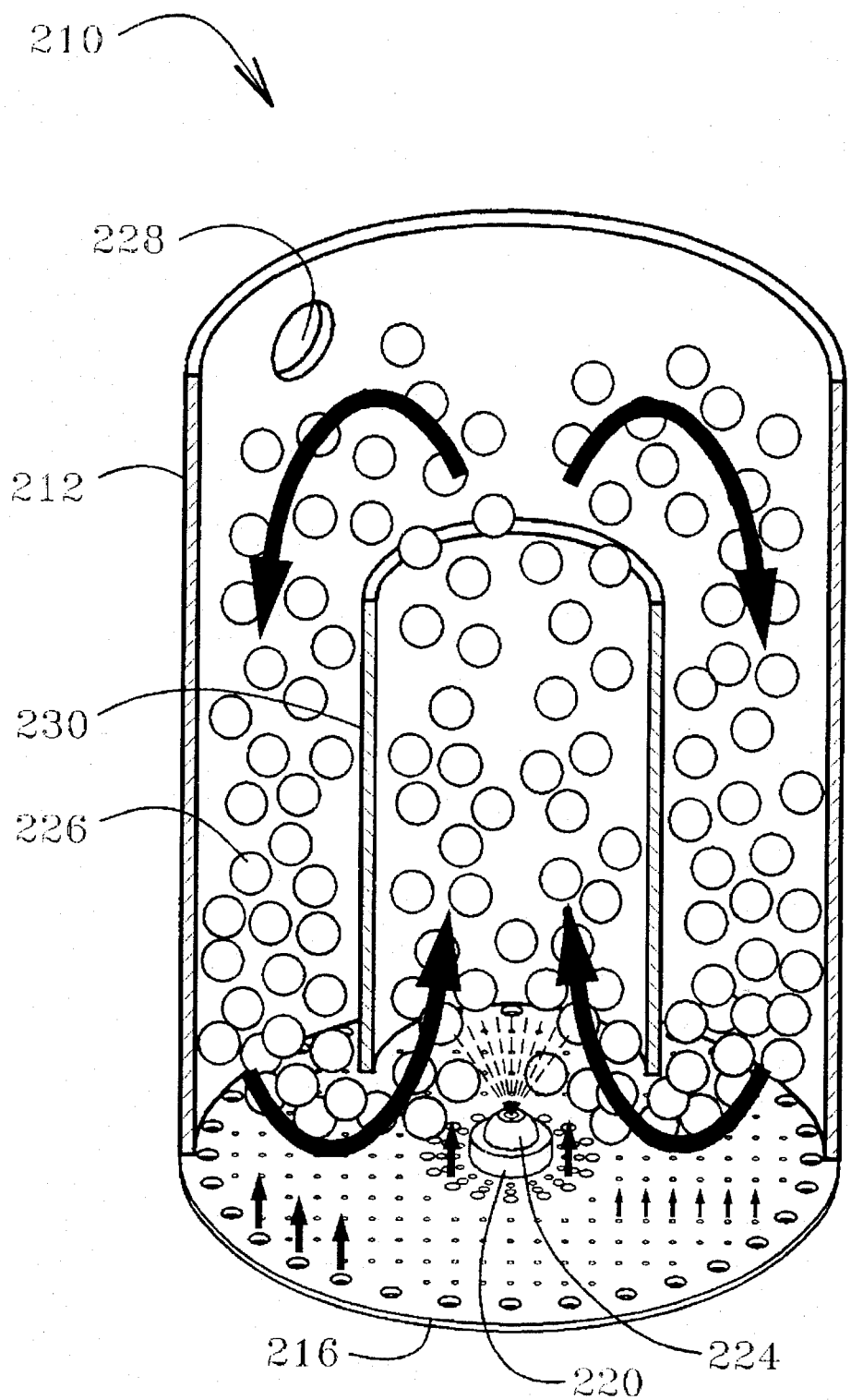
FIG. 3 is a cross sectional view of an air suspension chamber for encapsulating the microspheres of the invention.

Using the apparatus of FIG. 3, the microspheres prepared as in Examples 1–22 were encapsulated with two or more layers of various encapsulant compositions to produce microcapsules. The enteric coatings were dissolved in a solvent mixture, as shown, to which was optionally added a dyestuff, FD&C #1 Lake Blue, or FD&C #6 Lake Yellow. EUDRAGIT E-100 provides stability in liquid suspension and in the mouth, (pH about 7) and is soluble in the stomach (pH less than 5.5). EUDRAGIT L-100-55 will provide protection in the stomach and release the drug in the intestinal tract (pH over 5.5).

The data relating to the application of the coatings are summarized in Table IV below.

TABLE IV

| Example | Microsphere Example | Shell Coating Composition % By Weight | | | | | Colorant | | Assay; Microcapsules |
|---|---|---|---|---|---|---|---|---|---|
| | | Eudragit™ L-100-55 | Eudragit™ E-100 | Ethanol | Acetone | Methylene Chloride | #1 | #6 | |
| 35 | 14 | 4 | | 19.2 | 76.8 | | 0.1 | | |
|    |    |   | 4 | 24.0 |      | 72.0 |     | 0.1 | 17.2 |
| 36 | 2  | 4 |   | 19.2 | 76.8 |      | 0.1 |     | 25.6 |
|    |    |   | 4 | 24.0 | 72.0 |      |     | 0.1 |      |
| 37 | 3  | 4 |   | 24.0 | 72.0 |      | 0.1 |     | 25.4 |
|    |    |   | 4 | 24.0 |      | 72.0 |     | 0.1 |      |
| 38 | 4  | 4 |   | 24.0 | 72.0 |      | 0.1 |     | 26.7 |
|    |    |   | 4 | 24.0 |      | 72.0 |     | 0.1 |      |
| 39 | 4  | 4 |   | 24.0 | 72.0 |      | 0.1 |     | 24.2 |
|    |    |   | 4 | 24.0 | 72.0 |      |     | 0.1 |      |
| 40 | 6  | 4 |   | 24.0 | 72.0 |      | 0.1 |     | 24.5 |
|    |    |   | 4 | 24.0 | 72.0 |      |     | 0.1 |      |
| 41 | 7  | 4 |   | 24.0 | 72.0 |      | 0.1 |     | 25.2 |
|    |    |   | 4 | 24.0 | 72.0 |      |     | 0.1 |      |
| 42 | 8  | 4 |   | 24.0 | 72.0 |      | 0.1 |     | 26.0 |
|    |    |   | 4 | 24.0 | 72.0 |      |     | 0.1 |      |
| 43 | 9  | 4 |   | 24.0 | 72.0 |      | 0.1 |     | 26.0 |
|    |    |   | 4 | 24.0 | 72.0 |      |     | 0.1 |      |
| 44 | 10 | 4 |   | 24.0 | 72.0 |      | 0.1 |     | 26.0 |
|    |    |   | 4 | 24.0 | 72.0 |      |     | 0.1 |      |
| 45 | 11 | 4 |   | 24.0 | 72.0 |      | 0.1 |     | 25.6 |
|    |    |   | 4 | 24.0 | 72.0 |      |     | 0.1 |      |
| 46 | 12 | 4 |   | 24.0 | 72.0 |      | 0.1 |     | 26.3 |
|    |    |   | 4 | 24.0 | 72.0 |      |     | 0.1 |      |
| 47 | 1  | 4 |   | 24.0 | 72.0 |      | 0.1 |     | 25.2 |
|    |    |   | 4 | 24.0 | 72.0 |      |     | 0.1 |      |

The data relating to the amount of the coatings applied is given below in Table V. where the result was obtained from a measurement of the amount of shell solution per weight of microsphere sample used during the coating process. The resultant microcapsules were in the 250 to 500 micrometer size range.

TABLE V

| | Weight % Shell | |
|---|---|---|
| Example | Inner | Outer |
| 36 | 14.0 | 13.9 |
| 43 | 13.0 | 13.3 |
| 44 | 13.0 | 13.8 |
| 45 | 13.0 | 13.2 |
| 46 | 13.0 | 13.1 |
| 47 | 13.0 | 13.6 |

EXAMPLE 48

Microcapsule samples made as in Examples 35–47 were evaluated for stability in simple syrup solution by storing for 1 and 4 weeks under accelerated shelf-life conditions at 37° C. The amount of antibiotic found in the syrup was determined. The data are summarized below in Table VI.

TABLE VI

| Microcapsules, Example | % Release 1 Week | % Release 4 Weeks |
|---|---|---|
| 35 | <1.0* | 6.2 |
| 36 | 0.11 | 2.4 |
| 37 | <1.0* | 2.5 |
| 38 | <1.0* | 2.5 |
| 39** | <1.0* | 3.0 |
| 40 | 0.97 | 2.6 |
| 41 | 0.74 | 2.0 |
| 42 | 1.3 | 2.9 |
| 43 | 0.76 | 3.1 |
| 44 | 0.74 | 2.0 |
| 45 | 0.81 | 2.2 |
| 46 | 0.74 | 1.9 |
| 47 | 0.64 | 1.6 |

*Estimated
**These samples were then shaken at 37° C. for 48 hours. The % release for Example 39 was 3.6%; the % release for Example 47 was 1.8%.

It is apparent that the microcapsules of the invention are stable in aqueous solution for long periods of time, even under accelerated temperature conditions.

EXAMPLE 49

Part A

Microspheres were made following the procedure of Example 1 using 40.0% of erythromycin ethyl succinate within a 60% Durkee 17 matrix. The matrix temperature was 235° F.

The product contained 39.4% of particles 106–250 micrometers in size; and 60.4% of particles 250–355 micrometers 10 in size.

The actual amount of the antibiotic found in the microspheres was 31.2%.

Part B

The procedure of Example 35 was followed to make microcapsules of the microspheres of Part A. The first coating was made using EUDRAGIT L-30D and a second coating of EUDRAGIT E-100 using a solvent mixture of 72.0 parts of methyLene chloride and 24.0 parts of ethanol. The microcapsules contained 20.0% of erythromycin ethyl succinate.

EXAMPLES 50–55

The procedure of Example 1 was followed to prepare microspheres except that the drug employed was amoxicillin trihydrate in varying amounts. The data on microsphere preparation is summarized below in Table VII.

TABLE VII

| Example | Matrix Composition | Temp. °F. | Particle Size, Micrometers | Weight % | % Amoxicillin Trihydrate Theoretical | Found |
|---|---|---|---|---|---|---|
| 50 | 44.1% E6349 18.9% D17 7.0% Al St | 170 | 250–355 | 100 | 30.0 | 24.0 |
| 51 | 50.4% E6349 12.6% Tallow Flakes | 200 | 106–250 250–355 | 35.9 64.1 | 37.0 | Not-Tested |
| 52 | 63.0 D17 | 200 | 250–355 | 100 | 37.0 | 32.5 |
| 53 | 63.0% D17 | 210 | 106–250 250–355 | 50.8 49.2 | 32.0 | 26.7 |
| 54 | 68.0% D17 | 200 250–355 | 106–250 49.2 | 50.8 | 32.0 | 26.7 |
| 55 | 68.0% D17 | 200 | 250–355 | 100 | 32.0 | 21.8 |

EXAMPLES 56–60

The microspheres as in Examples 50–55 were encapsulated following the procedure of Example 35. The data relating to the encapsulations are summarized in Table VIII below:

TABLE VIII

| Example | Microsphere Example | Shell Coatings, % By Weight | | | Solvent | | | Colorant | | Assay; Microcapsules |
| | | Eudragit™ L-100-55 | Eudragit™ E-100 | Eudragit™ L-30D | Ethanol | Acetone | Methylene Chloride | #1 | #6 | |
|---|---|---|---|---|---|---|---|---|---|---|
| 56 | 50 | 4 | | | 24.0 | 72.0 | | 0.1 | | |
| | | | 4 | | 24.0 | 72.0 | | | 0.1 | 21.6 |
| 57 | 51 | 4 | | | 24.0 | 72.0 | | 0.1 | | — |
| 58 | 52 | | 4 | | 24.0 | | 72.0 | | | 15.9 |
| | | | | 100 | | | | 0.1 | | |
| | | | 4 | | 24.0 | | 72.0 | | 0.1 | |

TABLE VIII-continued

| | Shell Coatings, % By Weight | | | | Solvent | | | Colorant | | Assay; |
|---|---|---|---|---|---|---|---|---|---|---|
| Example | Microsphere Example | Eudragit ™ L-100-55 | Eudragit ™ E-100 | Eudragit ™ L-30D | Ethanol | Acetone | Methylene Chloride | #1 | #6 | Microcapsules |
| 59 | 54 | | 4 | | 24.0 | | 72.0 | | | — |
| 60 | 55 | | 4 | | 24.0 | | 72.0 | | 0.1 | 16.4 |
| | | | | 100 | | | | 0.1 | | |
| | | | 4 | | 24.0 | | 72.0 | | 0.1 | |

EXAMPLE 61

The microcapsule samples made as in Example 56 using the microspheres as made in Example 50 were evaluated in simple syrup solution by storing for one, four and eleven weeks under accelerated shelf life conditions at 37° C. The amounts of antibiotic found in the syrup after vigorous shaking is as follows: 0.0% release after one week; 3.1% release after four weeks and 26.5% release after eleven weeks.

It is apparent that the microspheres of the invention can be encapsulated with multiple coatings as desired using the processes of the invention. The resultant microcapsules are small in size, are water impervious, and can be tailored so that the drug is protected in aqueous solutions, and can be released as desired, and when desired, to optimize the drug's effectiveness. The invention also provides a means of dispensing a water unstable drug in an aqueous solution that is stable and which can be stored at room temperature for extended periods of time.

I claim:

1. A method for producing drug delivery microcapsules having successive, systemic environment-activated release phases comprising the steps of:

selecting a microsphere core particle;
   encapsulating said core particle in a first coating formed of a first coating material which first material, prior to dissolution, is liquid impervious, is water insoluble at a pH of less than about 5.5, but water soluble at a pH greater than 5.5; and
   encapsulating said core particle and said first coating with a second coating formed of a second coating material which is water insoluble at neutral pH but soluble at a pH of less than 5.5.

2. The method of claim 1 wherein said core particle is of a drug which is unstable in water.

3. The method of claim 1 wherein said core particle, with said first and second coatings applied thereto is less than about 1500 micrometers in any dimension.

4. Method of claim 2, wherein the water-unstable drug is ampicillin, amoxicillin, penicillin V, or the salts, esters or hydrates thereof.

5. The method of claim 1, wherein the microsphere core particles comprise a water-unstable drug in a matrix of a lipid selected from the group consisting of partially hydrogenated vegetable oils, stearic acid, hydrogenated allow triglycerides, food grade metal stearates, tallow and mixtures thereof.

6. The method of claim 1 wherein said first material comprises a polymethacrylic acid or a polymethacrylic acid ester.

7. The stable dosage form of claim 1, wherein each microcapsule has a particle size of 250 to 550 micrometers.

8. The stable dosage form of claim 1, wherein each microsphere core particle has a particle size of 105 to 500 micrometers.

9. The method of claim 1, wherein each microsphere core particle has a particle size of 250 to 355 micrometers.

* * * * *